United States Patent [19]
Schulz et al.

[11] Patent Number: 5,515,160
[45] Date of Patent: May 7, 1996

[54] METHOD AND APPARATUS FOR REPRESENTING A WORK AREA IN A THREE-DIMENSIONAL STRUCTURE

[75] Inventors: Hans-Joachim Schulz; Hanns-Peter Tümmler; Paul Wieneke, all of Tuttlingen, Germany

[73] Assignee: Aesculap AG, Tuttlingen, Germany

[21] Appl. No.: 302,676

[22] PCT Filed: Feb. 20, 1993

[86] PCT No.: PCT/EP93/00409

§ 371 Date: Sep. 9, 1994

§ 102(e) Date: Sep. 9, 1994

[87] PCT Pub. No.: WO93/18426

PCT Pub. Date: Sep. 16, 1993

[30] Foreign Application Priority Data

Mar. 12, 1992 [DE] Germany .......................... 42 07 901.2

[51] Int. Cl.⁶ .................................................. G02B 23/26
[52] U.S. Cl. ............................................ 356/241; 600/117
[58] Field of Search ...................... 356/372, 375, 356/376, 241; 359/368; 600/101, 103, 109, 114, 117, 118, 175; 348/65, 66, 68, 79; 250/560, 561

[56] References Cited

U.S. PATENT DOCUMENTS

| | | | |
|---|---|---|---|
| 4,588,294 | 5/1986 | Siegmund | 356/241 |
| 4,660,982 | 4/1987 | Okada. | |
| 4,722,056 | 1/1988 | Roberts et al. | 364/413 |
| 4,902,129 | 2/1990 | Siegmund et al. | 356/241 |
| 4,980,763 | 12/1990 | Lia | 600/117 |

FOREIGN PATENT DOCUMENTS

| | | |
|---|---|---|
| 0352952 | 1/1990 | European Pat. Off. . |
| 3405909 | 8/1985 | Germany . |
| 3411140 | 9/1985 | Germany . |
| 3516164 | 11/1985 | Germany . |
| 4038125 | 6/1992 | Germany . |
| WO90/05494 | 5/1990 | WIPO . |
| WO91/14397 | 10/1991 | WIPO . |

OTHER PUBLICATIONS

Bruce A. Kall, et al., "The Computer as a Stereotactic Surgical Instrument," *Neurological Research*, vol. 8, Dec. 1986, pp. 201–208.

U. Breitmeier: "Einsatz opto–elektronischer Sensoren in der Fertigungsmesstechnik sowie zum steuern von Roboten," *VDI–Zeitung*, vol. 125 (1983) No. 21, pp. 873–879.

Patent Abstracts of Japan—Abstract No. JP1223926, vol. 13 No. 546, Jun. 12, 1989.

*Primary Examiner*—Hoa Q. Pham
*Attorney, Agent, or Firm*—Barry R. Lipsitz

[57] ABSTRACT

In order to ensure, in a process for representing a work area in a three-dimensional structure in which the work area is imaged by a viewing device, that the viewing device or an instrument can be introduced into the structure along a predetermined path of displacement despite the different positioning of the viewing device, it is suggested that the relative positioning of the viewing device is determined relative to the structure, that the coordinates of a path of displacement are predetermined for an instrument or for the viewing device in the structure, are compared with the respective positioning and the path of displacement is represented in its correct position in the image. A device for performing this process is also described.

18 Claims, 1 Drawing Sheet

METHOD AND APPARATUS FOR REPRESENTING A WORK AREA IN A THREE-DIMENSIONAL STRUCTURE

BACKGROUND OF THE INVENTION

The invention relates to a process for representing a work area in a three-dimensional structure in which the work area is imaged by a viewing device.

The invention further relates to a device for representing a work area in a three-dimensional structure with a viewing device of the work area.

When viewing three-dimensional structures with viewing devices, i.e. for example with endoscopes or microscopes, a plane extending vertically to the optical axis of the viewing device and arranged in the focal plane of the viewing device is sharply imaged by the viewing devices so that a viewer can view a plane of the three-dimensional structure either directly or indirectly by the interposition of a camera and a monitor. In this respect, the three-dimensional structure can be anything desired, for example, it can be the interior of a machine, a biological preparation or a human or animal body. These structures are often exceptionally complicated, so that it is favorable not to decide only at the actual viewing of the structure how the viewing device or an instrument is to be advanced in the structure in order to reach a certain point, but it has proven to be favorable to plan the advance path beforehand.

The object is to develop a process of the generic type such that when viewing a three-dimensional structure, the path of displacement planned in advance for the viewing device or for an instrument becomes immediately visible for the viewer so that he can directly control the advancing movement of the viewing device or an instrument when viewing the structure.

SUMMARY OF THE INVENTION

This object is accomplished in accordance with the invention, in a process of the type described at the beginning, in that the relative positioning of the viewing device is determined relative to the structure, that the coordinates of a path of displacement are predetermined for an instrument or for the viewing device in the structure, are compared with the respective positioning and the path of displacement is represented in its correct position in the image of the work area.

In a first preferred embodiment, the procedure is such that one plane of the structure after the other is imaged each time with the viewing device and that the piercing point or points of the path of displacement in the observed plane is/are represented in the correct position in the image of the respectively observed plane.

By means of an exact measurement of the relative positioning of the viewing device relative to the structure, it can be determined exactly which plane in the structure is imaged in the viewing device, namely a plane lying in the focal plane of the viewing device and extending vertically through the optical axis of the viewing device. Thus, for every desired relative position of the viewing device relative to the structure, another plane is sharply imaged.

After this plane has been determined, the point of intersection of this plane with a predetermined path of displacement in the structure can be calculated and it can thereby be determined exactly in which position of the imaged plane the predetermined path of displacement penetrates this plane. When the optical axis of the viewing device is arranged exactly in the piercing point of the predetermined path of displacement, this piercing point is located in the middle of the observed surface, in a lateral deviation of the path of displacement from the optical axis, at a distance from the central point of the image. It is customary when observing the planes to indicate the position of the optical axis, for example, by a Graticule so that in other words, due to the determination of the position of the observed plane and the comparison of the coordinates of this plane with the coordinates of the predetermined path of displacement, the distance and the direction, which have to be covered by the graticule in order to reach the piercing point of the path of displacement in the observed plane, can be determined.

This piercing point in the observed plane is additionally represented in the process according to the invention, for example, by superimposition on a monitor or by blending in a correspondingly positioned picture or image in the beam path of the microscope. Thus, the viewer can simultaneously observe the picture of the imaged plane actually transmitted by the viewing device and a marking which indicates the piercing point of the predetermined path of displacement through this plane.

When the path of displacement is determined for the displacement movement of the viewing device itself, the viewing device can be positioned relative to the structure by lateral displacement of this viewing device such that the piercing point is arranged in the optical axis, i.e. the viewer moves the viewing device relative to the structure until the marking of the piercing point coincides with the graticule in the image. If this takes place in every plane, then it is ensured that the optical viewing device is moved along the predetermined path of displacement.

If the path of displacement is determined for an instrument, then the user observes the actual position of the instrument in the observed plane and moves the instrument sideways such that it coincides with the marking of the piercing point. If this results in all planes, then it is ensured that the instrument is guided along the predetermined path of displacement. In this respect, it is essential that such a guidance of the instrument along the path of displacement is not dependent on how the viewing device is exactly arranged relative to the structure, since due to the constant measurement of the relative position of the viewing device relative to the structure and by the comparison of the set of data attained thereby with the coordinates of the predetermined path of displacement, a corresponding change of the distance and the direction of the marked point from the graticule also results, so that the relative position of the piercing point relative to the momentary focal point of the viewing device is always displayed.

In the described process, one plane after the other must be observed in order to correct the displacement movement of an instrument or the viewing device, whereby the piercing points migrate in correspondence with the predetermined path of displacement. In a preferred embodiment, the piercing point or points of the path of displacement of at least one of the planes adjoining the viewing plane is/are represented additionally, next to the piercing points of the path of displacement in each represented plane. Thus, in the observed representation, not only are the piercing points in the observed plane represented but also piercing points in a parallel plane lying thereover or thereunder, for example. When the path of displacement extends vertically to the planes, only a marking results as before; however, when it is inclined with respect to the observed planes, the corresponding marking points lie next to each other in the representation. Thus, the observer can also recognize in which direction, for example, an instrument has to be moved when the instrument is displaced vertically to the observed plane into a plane lying lower or a plane lying higher. This can be the case for a great number of planes, so that the path of displacement is actually projected into the observed plane.

In this respect, it is favorable when the piercing points of different planes are connected by a line in the representation.

Furthermore, it is advantageous when the piercing point or points through the observed plane is/are represented differently to piercing points in other planes. This facilitates the displacement of the instrument or the observing device.

In the process described above in detail, the plane of the work structure imaged by the viewing device is imaged two-dimensionally; consequently, piercing points of the path of displacement through this plane or the projection of the planned path of displacement into this plane are represented.

In a modified embodiment, the work area can be viewed stereoscopically and imaged three-dimensionally and the path of displacement is superimposed in its correct position as three-dimensional representation of the three-dimensional image of the work area. This can result, for example, by means of stereoscopical viewing known per se in which two separate images are superimposed which give the viewer a three-dimensional impression. A picture can be incorporated in a suitable manner in the beam path, this picture also representing the desired path of displacement three-dimensionally which is seen in its correct position in the actual three-dimensional image. In this respect, it can be proceeded in a similar manner, as is known, for example, from display instruments for aircraft with which pictures appearing three-dimensionally are produced at a certain position also in the field of vision of the viewer.

In this respect, it is advantageous when the path of displacement is marked in the piercing point of the plane of observation extending through the focal point of the viewing device, for example, by means of different colors or different brightness. This shows the viewer the location of the sharply imaged plane of the work area; simultaneously, he can see the regions of the work area lying thereover and thereunder three-dimensionally and the course of the path of displacement in this region.

The coordinates of the path of displacement can, for example, be determined by means of a plurality of sectional plane representations of the structure and piercing points of the path of displacement determined therein.

Thus, the corresponding structures can be preliminarily examined in a conventional manner with the aid of an X-ray tomograph or a nuclear spin tomograph, i.e. sectional view representations of the structure are produced. The desired paths of displacement are defined in these sectional view representations or in the corresponding sets of data, i.e. the coordinates of the piercing points of the path of displacement are determined in these planes. When putting these data together, then a three-dimensional set of data is obtained which describes the path of displacement within the structure from the beginning to the end.

This set of data is compared in the described manner with the data which describe the respective positioning of the viewing device relative to the structure and with that, the position of the observed plane in the structure.

The mentioned object is solved further by a device of the type described in the beginning, which is characterized by a measuring means for determining the position of the viewing device relative to the structure, by a comparator for comparing the position data of the viewing device valid for each observed plane with the coordinates of a predetermined path of displacement of the work area and by a display unit which images the predetermined path of displacement in its correct position in the work area.

In a first preferred embodiment, the viewing device sharply images one plane of the work area and the piercing point of the path of displacement is imaged in its correct position in the observed plane.

In this respect, it is advantageous when the display unit additionally displays the piercing point or points of the path of displacement of at least one of the planes adjoining the viewing plane, next to the piercing points of the path of displacement in each represented plane.

Furthermore, it is expedient when the display unit connects the piercing points of different planes by a line in the representation.

In a preferred embodiment, the display unit represents the piercing point or points through the observed plane differently to piercing points in other planes.

In another type of embodiment, the viewing device images a work area three-dimensionally and the predetermined path of displacement is superimposed in its correct position as three-dimensional representation of the three-dimensional image of the work area.

In this respect, it is favorable when the path of displacement is marked the piercing point of the viewing plane extending through the focal point of the viewing device, for example, by a different color or a different brightness.

In a preferred embodiment, the comparator has a data memory in which a set of data is stored for the path of displacement relative to the structure.

The following description of a preferred embodiment of the invention serves to explain the invention in greater detail in conjunction with the drawings.

DETAILED DESCRIPTION OF THE INVENTION

Figure 1:
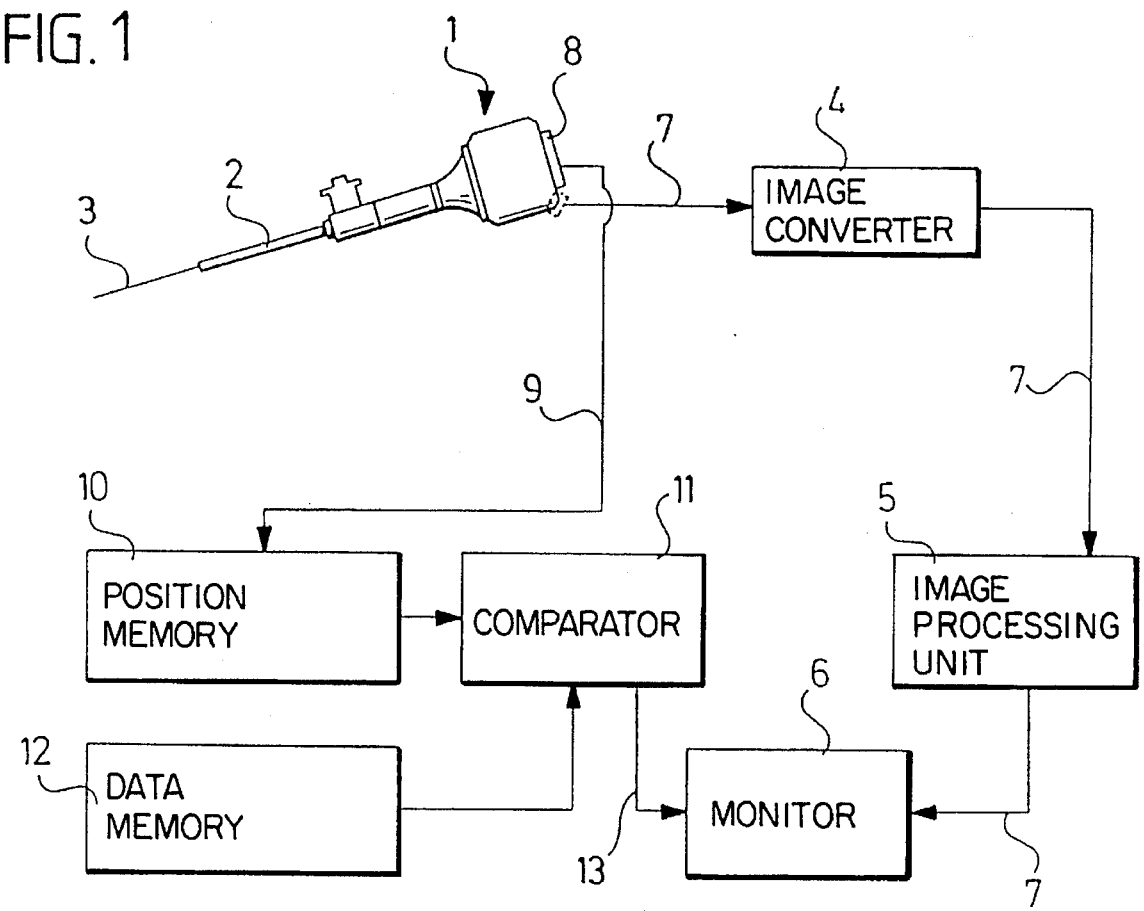
FIG. 1 is a schematic representation of an observing device with a position measuring means and a device for imaging the desired path of displacement in its correct position and FIG. 2 is a representation of the image observable by the observer with a representation of the predetermined path of displacement and a representation of an instrument.

In the illustration of FIG. 1, an endoscope 1 is used to view a structure to be examined which is not illustrated in the drawing. The endoscope 1 has in a tube 2 an optical means not illustrated in detail, which has a focal plane at a certain distance in front of the end of the tube 2. In the embodiment represented in the Figure, an instrument 3 in the form of a tip is held at the tube 2 and terminates in the focal plane. The instrument 3 thus marks the focal point of the optical viewing means with its front end and is simultaneously used as scanning instrument, as electrode, as probe or the like.

The light transferred by the optical system of the endoscope 1 is converted in an image converter 4 into electric signals which are supplied to a monitor 6 via a line 7 after corresponding image processing in an image processing unit 5, the surface viewed by means of the endoscope 1 being represented on this monitor.

The image can be processed electronically in the image processing unit 5 in a manner known per se, for example, by contrast increase, by special coloration techniques or by enlargements, etc.

The exact positioning of the endoscope 1 relative to the structure to be viewed is determined by means of suitable sensors 8 and the position signals generated thereby are supplied to a position memory 10 via a line 9. The sensors 8 can, for example, be ultrasonic transmitters, which act together with corresponding ultrasonic microphones on the structure so that the relative positioning can be determined by means of different cycle measurements.

The signals determining the respective positioning are supplied from the position memory 10 to a comparator 11 which, in addition, is provided with sets of data from a data memory 12 by means of which the coordinates of the desired path of displacement of the endoscope or an instrument in the structure to be viewed are described.

These sets of data are acquired by foregoing structure stipulations and by specifying the desired path of displacement in the structure determined in this manner.

Figure 2:
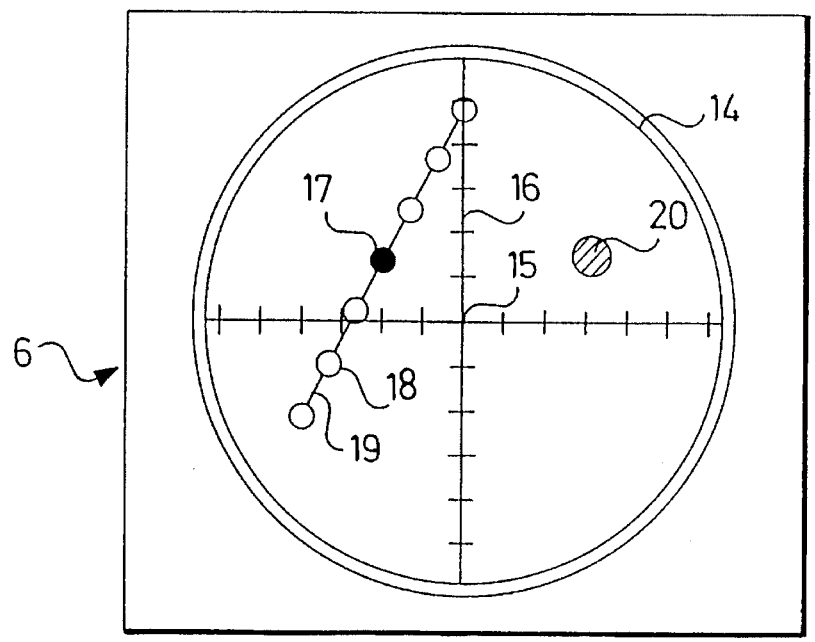

In the comparator 11, the position data of the endoscope 1 are compared with these sets of data of the desired path of displacement, so that it can be determined exactly at which point of the observed plane the path of displacement penetrates this plane. Corresponding data can be determined likewise in the comparator 11 for the planes which lie above or below the viewed plane so that corresponding coordinates are made available for the different piercing points of the path of displacement and these planes. These coordinates are transmitted via a line 13 to the monitor 6 and lead to the marking of the corresponding coordinates of the piercing point in the represented plane, i.e. a picture of such a marking with the image directly attained by the endoscope 1, results. In FIG. 2, a possible picture of a monitor representation is illustrated. The entire visual range attainable by the endoscope 1 is enclosed in a circle 14, the central point 15 of which is marked by a graticule 16.

The central point 15 coincides with the optical axis of the endoscope 1 so that an image of the structure is produced within the circle 14 in the plane which lies vertically on the optical axis and coincides with the focal plane of the endoscope 1. In this respect, the central point 15 marks the piercing point of the optical axis through this plane.

In addition, in the region enclosed by the circle 14, several additional markings are recognized, namely a solid dot 17 and several circular dots 18, which are all interconnected with each other by a line 19.

The solid dot 17 marks the piercing point of the predetermined and desired line of displacement through the viewed plane, the circles 18 on the one side of the dot 17 mark corresponding piercing points in parallel planes lying above the viewed plane and the circles on the other side of the dot 17 mark corresponding piercing points in parallel planes lying below the viewed plane. Thus, by means of the circles 18 and the dot 17, a projection of the path of displacement onto the viewed plane is represented, whereby the piercing point of the path of displacement is marked by the dot 17.

The position in which the circles and dots are represented on the monitor results from the set of data of the predetermined path of displacement. By means of the position measurement of the endoscope 1, the position of the observed plane can be described mathematically, so that by mathematically intersecting the path of displacement and this plane, the piercing point can be calculated, i.e. the distance from the optical axis and the angle in relation to a certain direction. These data are sufficient to image the piercing point on the monitor.

When the user, for example, wants to guide the instrument 3 along the predetermined path of displacement he recognizes from the representation of FIG. 2 that the tip of the instrument, which coincides with the optical axis and is thereby marked by the graticule 16, is at a distance from the piercing point of the desired path of displacement. By moving the endoscope and the instrument held thereon, the user can cause the dot 17 on the monitor picture to be displaced into the graticule. If this is achieved, then it is ensured that the tip of the instrument penetrates the observed plane exactly in the piercing point of the path of displacement, i.e., is positioned in the desired manner. When the endoscope is pushed further into the structure, planes lying thereunder are reached which are then represented, whereby the circles 18 already indicate to the user before the endoscope is moved into a deeper position, in which direction the endoscope is to be moved sideways in order to be guided further along the path of displacement. Thus, the user can move the tip of the instrument 3 along the path of displacement when inserting the endoscope, if he endeavors to always keep the respective dot 17, which is obviously different for each viewed plane, in the graticule.

In another embodiment in which a separate instrument is used, the piercing point of this instrument through the observed plane is observable on the monitor. This piercing point is characterized with the reference numeral 20 in the illustration of FIG. 2.

In order to ensure that this instrument is always moved along the desired path of displacement, the instrument has to be moved sideways until the piercing point coincides with the marked dot 17 in the representation. With this, it is guaranteed that the piercing point of the instrument through the observed plane lies on the desired path of displacement. However, with this it is not guaranteed that the slide-in depth of the instrument is also correct; for this, additional measures ought to be found, if necessary, for example a certain design of the instrument only at its end region so that this certain form can be monitored, since the end of the instrument is just located in the respectively observed plane.

In this manner of use, the endoscope must not necessarily follow the path of displacement, but it can also take another path, since it is ensured by means of the respective position measurement of the endoscope and by comparing the sets of data, that the piercing point of the path of displacement is displayed at the right location every time the endoscope is positioned in the respectively observed plane.

When the described device is used, for example, when operating on a human being, the three-dimensional form of the body, i.e. the structure, is firstly determined by a plurality of sectional views before the operation with the body not yet opened, by conventional techniques, for example, by customary computer tomography or by nuclear spin tomography. In the corresponding sectional views, the desired path of displacement, i.e. the respective piercing point of the path of displacement, can be inserted into each plane so that in this manner, by means of interpolation, a set of data for the description of the three-dimensional structure is obtained, on the one hand, and on the other hand, a further set of data for the coordinates of the path of displacement in this structure.

In the actual operation, the endoscope and, if necessary, an additional instrument, is inserted into the body through openings in the body. The respective plane of the structure lying in the focal plane of the endoscope is imaged on the monitor. In addition, the piercing point of the predetermined path of displacement through the observed plane is recognized on the monitor, i.e. the operator can, for example, ensure by moving the endoscope sideways that the latter is inserted into the structure precisely on the predetermined path of displacement. This correction can result in every desired plane by means of the dot 17; the circles 18 show the operator further in which direction the endoscope is to be moved during further insertion in order to remain along the desired path of displacement also in planes lying thereunder.

Hereinabove, the invention has been described on the basis of a two-dimensional representation of the work area wherein one plane of the work area lying in the focal plane of the viewing-device is sharply imaged each time. In one embodiment not expressly represented in the drawing, this can be modified such that an image of the work area appearing three-dimensionally is produced, for example, by means of a stereoscopic view through superposition of two slightly different sectional images. The predetermined path of displacement is likewise three-dimensionally superimposed on this image appearing three-dimensionally, so that the viewer can observe the course of the path of displacement in the work area over a certain layer thickness of the same. Advantageously, the piercing point of the path of displacement through the plane lying in the focal plane of the viewing device is marked either by a different color, a different brightness or a different form, e.g. a thickening. Fundamentally, in this application of the invention, it is, however, essential to the same extent that the positioning of the viewing device is constantly measured in relation to the three-dimensional structure and in response to this measurement, the data of the path of displacement stored in a memory is transferred to the representation in the correct position.

We claim:

1. A method for representing a work area in a three-dimensional structure, comprising the steps of:

providing an image of said work area via a viewing device;

determining the position of said viewing device or an instrument movable therewith relative to said structure;

comparing the determined position of said viewing device or instrument to a set of coordinates of a predetermined path of displacement therefor in said structure; and representing said predetermined path of displacement in said image as a piercing point through respective observed planes of said structure to enable said viewing device or instrument to be guided generally along said predetermined path.

2. A method in accordance with claim 1 comprising the further step of representing the piercing point along said path for at least one plane in addition to the plane currently being observed.

3. A method in accordance with claim 2 wherein said at least one additional plane adjoins the plane currently being observed, and a set of piercing points for the adjoining planes is shown next to one another in said image.

4. A method in accordance with claim 3 wherein the piercing points of different planes are illustrated in said image as being connected by a line.

5. A method in accordance with claim 4 wherein the piercing point of the plane being observed is represented differently from the piercing point(s) shown in said image for other planes.

6. A method in accordance with claim 3 wherein the piercing point of the plane being observed is represented differently from the piercing point(s) shown in said image for other planes.

7. A method in accordance with claim 3 wherein the coordinates of said path of displacement are determined from a plurality of sectional plane representations of said structure and a set of piercing points of the path of displacement in these representations.

8. A method in accordance with claim 2 wherein a set of piercing points of different planes is illustrated in said image as being connected by a line.

9. A method in accordance with claim 8 wherein the piercing point of the plane being observed is represented differently from the piercing point(s) shown in said image for other planes.

10. A method in accordance with claim 8 wherein the coordinates of said path of displacement are determined from a plurality of sectional plane representations of said structure and a set of piercing points of the path of displacement in these representations.

11. A method in accordance with claim 2 wherein the piercing point of the plane being observed is represented differently from the piercing point(s) shown in said image for other planes.

12. A method in accordance with claim 11 wherein the coordinates of said path of displacement are determined from a plurality of sectional plane respresentations of said structure and a set of piercing points of the path of displacement in these representations.

13. A method in accordance with claim 2 wherein the coordinates of said path of displacement are determined from a plurality of sectional plane representations of said structure and a set of piercing points of the path of displacement in these representations.

14. A method in accordance with claim 1 wherein said work area is imaged three-dimensionally and viewed stereoscopically, said path of displacement being superimposed in its correct position as a three-dimensional representation within the three-dimensional image of said work area.

15. A method in accordance with claim 14 wherein said path of displacement is marked in the piercing point of the plane of observation extending through a focal point of said viewing device.

16. A method in accordance with claim 14 wherein the coordinates of said path of displacement are determined from a plurality of sectional plane representations of said structure and a set of piercing points of the path of displacement in these representations.

17. A method in accordance with claim 1 wherein the coordinates of said path of displacement are determined from a plurality of sectional plane representations of said structure and a set of piercing points of the path of displacement in these representations.

18. Apparatus for representing a work area in a three-dimensional structure comprising:

a viewing device for sharply imaging a plane of the work area;

measuring means for determining a position of the viewing device relative to said structure;

a comparator for comparing position data of said viewing device determined by said measuring means with a set of coordinates of a predetermined path of displacement along a plurality of respective planes in the work area;

a display unit for displaying an image of one of said plurality of planes in said work area being observed by said viewing device; and a data memory for storing a set of data for said path of displacement relative to said structure;

wherein said display unit is responsive to said set of data for providing an image of a piercing point for the plane of said work area currently being observed by said viewing device, said piercing point being shown in its correct position along said path of displacement.

* * * * *